(12) United States Patent
Kuhn et al.

(10) Patent No.: US 6,436,935 B1
(45) Date of Patent: Aug. 20, 2002

(54) SEMI-SOLID AQUEOUS PREPARATIONS FOR ORAL APPLICATIONS OF TOLTRAZURIL SULPHONE

(75) Inventors: Matthias Kuhn, Rheinfelden; Bettina Rohde, Odenthal; Helmut Schnabel, Odenthal/Blecher; Hans-Christian Mundt, Erkrath, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/701,087

(22) PCT Filed: May 20, 1999

(86) PCT No.: PCT/EP99/03462

§ 371 (c)(1), (2), (4) Date: Nov. 22, 2000

(87) PCT Pub. No.: WO99/62519

PCT Pub. Date: Dec. 9, 1999

(30) Foreign Application Priority Data

Jun. 2, 1998 (DE) .......................................... 198 24 483

(51) Int. Cl.⁷ .......................... A01N 43/64; A61K 31/53
(52) U.S. Cl. ..................... 514/242; 514/241; 514/772.4; 514/772; 514/772.3; 424/489; 424/438

(58) Field of Search ................................. 514/241, 242, 514/772.4; 424/438, 439, 489; 426/2

(56) References Cited

U.S. PATENT DOCUMENTS

| | | | |
|---|---|---|---|
| 4,219,552 A | | 8/1980 | Haberkorn et al. ......... 424/249 |
| 5,883,095 A | * | 3/1999 | Granstrom et al. ......... 514/242 |
| 6,034,116 A | * | 3/2000 | Assmann et al. ........... 514/394 |

FOREIGN PATENT DOCUMENTS

| | | |
|---|---|---|
| DE | 2 718 799 | 11/1996 |
| DE | 19 519 821 | 12/1996 |
| EP | 0 116 175 | 8/1984 |
| WO | 98/43644 | 10/1998 |

* cited by examiner

*Primary Examiner*—Thurman K. Page
*Assistant Examiner*—Liliana Di Nola-Baron
(74) *Attorney, Agent, or Firm*—Joseph C. Gil; Godfried R. Akorli

(57) ABSTRACT

The present invention relates to orally administrable pastes of toltrazuril sulfone, comprising active compound in a concentration of 0.1–20% by weight, with a particle size of from 1 to $10 \cdot 10^{-6}$ m, polyacrylic acids having a degree of polymerization of about $3 \cdot 10^6$ in a concentration of 0.1–5% by weight and, if appropriate, preservatives and moisturizers, and the remainder to 100% by weight water.

3 Claims, No Drawings

SEMI-SOLID AQUEOUS PREPARATIONS FOR ORAL APPLICATIONS OF TOLTRAZURIL SULPHONE

The present invention relates to semisolid aqueous preparations for oral administration which comprise, as active component, 1-methyl-3-[4-[(trifluoro-methyl)sulphonyl] phenoxy]-m-tolyl]-s-triazine-2,4,6 (1H, 3H, 5H)-trione (=toltrazuril sulphone).

Toltrazuril sulphone is used as active compound in compositions for coccidioses and similar diseases in animals (U.S. Pat. No. 4,219,552, DE-P 2 718 799).

Usually, such compositions are solutions of the active compounds which are, after dilution with water, administered via the drinking water of the animals (EP-A 116 175). Such compositions are also powders and granules which are mixed with the feed of the untreated animals.

In cases where the active compound is only sparingly soluble in water, aqueous active compound suspensions are prepared using suitable suspending agents. To this end, the active compound is micronized in a wet grinding process and mixed with suspending agent and water. Semisolid or paste-like preparations are then prepared from such suspensions by adding thickeners. Micronization of toltrazuril sulphone by a wet grinding process leads to a product which cannot be processed any further. Thus, it is not possible to prepare a stable suspension of toltrazuril sulphone by customary methods. Accordingly, it was likewise not possible to prepare a paste comprising toltrazuril sulphone as active compound in a customary manner.

If toltrazuril sulphone is micronized in a dry process, the expected particle sizes of the active compound are such that a stable aqueous suspension of the active compound can only be achieved using very high concentrations of suspending agent.

However, compositions which are to be administered directly and without further dilution, such as, for example, oral pastes, should be prepared using as little additives as possible. However, a paste, prepared in the customary manner, of toltrazuril sulphone would, in addition to thickeners, have a high content of suspending agent.

The present invention relates to an orally administrable paste of toltrazuril sulphone, characterized in that a) the active compound, having a particle size of $1 \cdot 10^{-6}$ m and a particle size maximum of $50 \cdot 10^{-6}$ m, is present in a concentration of 0.1–20% by weight, b) polyacrylic acids having an acrylic acid content of 56% to 68% by weight and a molecular weight of about $3 \cdot 10^6$ and neutralized with alkali metal or alkaline earth metal bases, are present in a concentration of 0.1–5% by weight, c) optionally, moisturizers are present in a concentration of from 5 to 30% by weight, d) optionally, preservatives are present in a concentration of from 0.01 to 0.5% by weight, e) and the remainder to 100% by weight is made up with water.

In the formulations according to the invention, the active compound is preferably present in concentrations by weight of from 5% by weight to 20% by weight, particularly preferably from 10% by weight to 15% by weight.

The polyacrylic acids are preferably neutralized using alkali metal hydroxide or alkali metal carbonate. The formulation according to the invention comprises polyacrylic acids in concentrations by weight of from 0.2% to 1%, preferably of 0.5%. These are commercially available and known in pharmacopoeias, for example under the trade name Carbomer 934 P.

Preferred preservatives are para-hydroxybenzoic acid esters (parabenes) such as methyl 4-hydroxybenzoate, ethyl 4-hydroxybenzoate or propyl 4-hydroxybenzoate. To achieve sufficient preservation, the preservatives can be employed individually or in combination. Usually they are present in concentrations of 0.01–0.5% by weight.

The formulation may optionally also comprise moisturizers, such as, for example, glycerol or 1,2-propylene glycol. Moisturizers are used in concentrations by weight of from 5% to 30%, preferably from 10% to 20%.

The active compound is present in a particle size of from 1 to $10 \cdot 10^{-6}$ m, preferably from 1 to $5 \cdot 10^{-6}$ m. The particle size maximum is $50 \cdot 10^{-6}$ m, preferably $30 \cdot 10^{-6}$ m.

The desired particle size distribution of the active compound is achieved by dry grinding.

To this end, for example, 20 kg of active compound per hour are micronized in a flat-cylindrical air jet mill under a pressure of from 5 to 6 bar using pressurized air.

The composition according to the invention is obtained by mixing the individual components. Its consistency can be modified by increasing or reducing the water content. What is desired is a paste-like consistency. This permits oral administration of the composition with suitable applicators, such as syringes, tubes, spatulas, etc.

The compositions according to the invention are particularly suitable for combating coccidioses and similar diseases in a large number of mammals, such as equidae (horses, donkeys, etc.), ruminants (cattle, sheep, goats, camels or related species, etc.), pigs, dogs, cats, rabbits, rodents or other mammals. All age groups can be treated. Coccidioses and similar diseases are to be understood as meaning infections with infective stages of species of various genera, such as, for example, Eimeria, Isospora, Castoisospora, Sarkocystis, Toxoplasma, Neospora or Cryptosporidae. The treated animals can be final hosts or intermediate hosts. The resulting diseases vary (for example diarrhoea in the case of many coccidioses, disturbances of the locomotor system in the case of EPM, abortions, etc). Accordingly, the recommendations for use are very different. In general, dosages of up to 30 mg of active compound per kg body weight, administered once or repeatedly, are effective.

The paste can also be mixed under the animal feed.

EXAMPLE 1

Paste for Oral Administration or for Mixing Under the Feed Composition:

| | |
|---|---|
| Toltrazuril sulphone | 15 g |
| Polyacrylic acid | 0.5 g |
| Sodium hydroxide | 0.1 g |
| 1,2-Propylene glycol | 20 g |
| Propylparaben | 0.02 g |
| Methylparaben | 0.14 g |
| Water | q.s. 100 g |

Preparation

The components are stirred together. A semisolid aqueous preparation which can be filled into the appropriate applicators is formed.

What is claimed is:

1. Orally administrable paste of toltrazuril sulphone, characterized in that a) the active compound, having a particle size of $1–10 \cdot 10^{-6}$ m and a particle size maximum at $50 \cdot 10^{-6}$ m, is present in a concentration of 0.1–20% by weight, b) polyacrylic acids having an acrylic acid content of 56%–68% (by weight) and a molecular weight of about $3 \cdot 10^6$ and neutralized with alkali metal or alkaline earth metal bases, are present in a concentration of 0.1–5% by weight, c) optionally, moisturizers are present in a concentration of from 5 to 30% by weight, d) optionally, preservatives are present in a concentration of from 0.01 to 0.5% by weight, e) and the remainder to 100% by weight is made up with water.

2. A process for treating coccidia disease in animals comprising orally administering to the animals the paste according to claim 1.

3. Process for preparing the pastes according to claim 1, characterized in that the active compound is micronized and mixed with the other components.

\* \* \* \* \*